Figure 1:
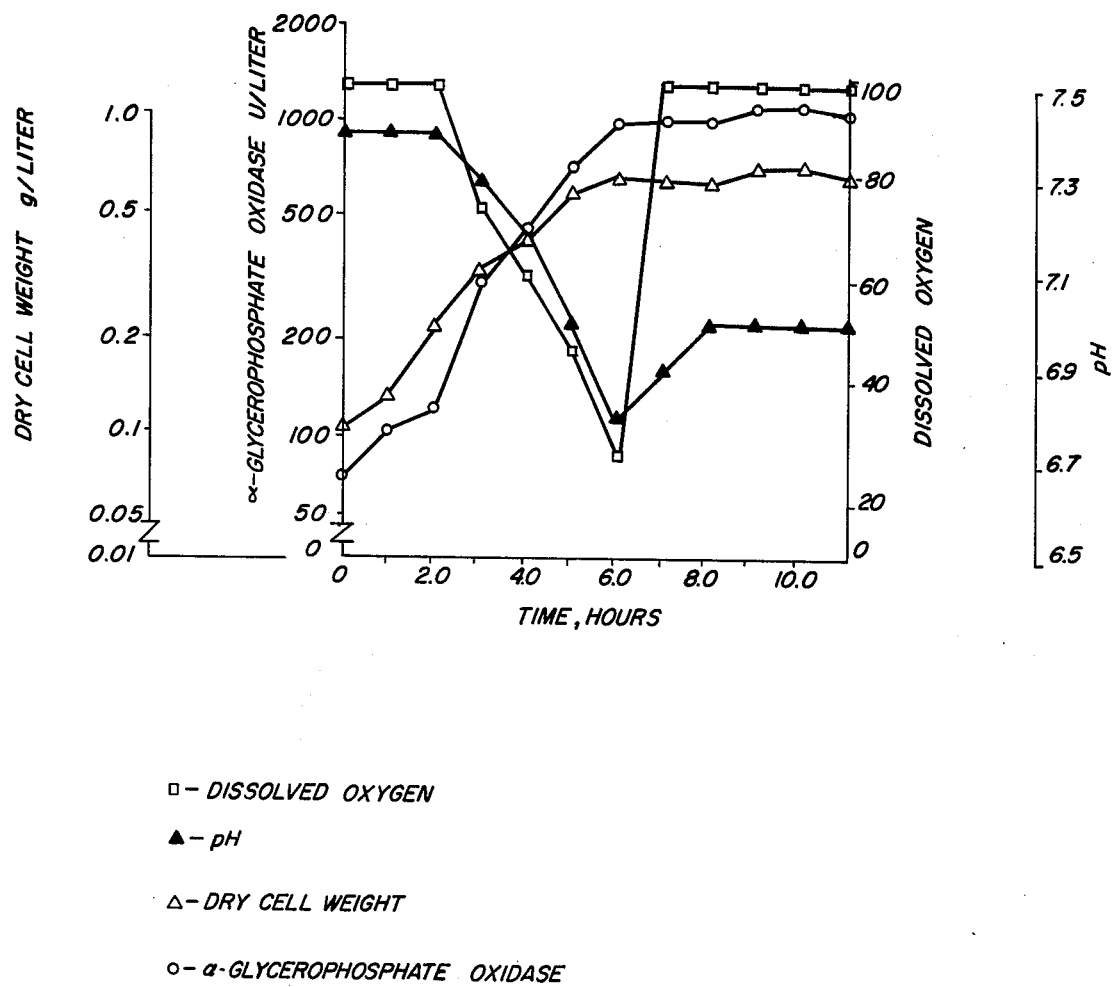

United States Patent [19]

Masurekar et al.

[11] 4,166,005

[45] Aug. 28, 1979

[54] PROCESS FOR THE PRODUCTION OF α-GLYCEROPHOSPHATE OXIDASE

[75] Inventors: Prakash S. Masurekar, Webster; Charles T. Goodhue, Rochester, both of N.Y.

[73] Assignee: Eastman Kodak Company, Rochester, N.Y.

[21] Appl. No.: 866,734

[22] Filed: Jan. 3, 1978

Related U.S. Application Data

[63] Continuation-in-part of Ser. No. 749,650, Dec. 10, 1976, abandoned.

[51] Int. Cl.$^2$ .............................................. C12D 13/10
[52] U.S. Cl. ...................., ........................ 435/190; 435/822; 435/853; 435/856; 435/857; 435/885
[58] Field of Search .................... 195/62, 65, 66 R, 96, 195/114

[56] References Cited

PUBLICATIONS

Koditschek et al., "α-Glycerophosphate Oxidase in *Streptococcus faecium* F24", *J. Bact.*, vol. 98, No. 3, pp. 1063–1068 (1969).
Jacobs et al., "The Purification and Properties of the α-Glycerophosphate Oxidizing Enzyme of *Streptococcus faecalis* 10Cl", *Arch. Biochem. Biophys.*, vol. 88, pp. 250–255 (1960).
Jacobs et al., "Comparison of the Mechanism of Glycerol Oxidation in Aerobically and Anaerobically Grown *Streptococcus faecalis*", *J. Bact.*, vol. 79, pp. 532–538 (1960).
Gunsalus et al., "The Oxidation of Glycerol by *Streptococcus faecalis*", *J. Bact.*, vol. 49, pp. 347–357 (1945).
Gunsalus, "Products of Anaerobic Glycerol Fermentation of *Streptococcus faecalis*", *J. Bact.*, vol. 54, pp. 239–244 (1947).
Claridge et al., "Oxidation of Glycerol by *Streptococcus faecalis*", *J. Bact.*, vol. 84, pp. 1181–1186 (1962).
Kamihara et al., "Pyruvate Oxidation and Related Metabolism in *Streptococcus faecalis*, II, The Physiological Role of Pyruvate Oxidation", *Chem. Abst.*, vol. 69, No. 13, p. 4664, Abs. No. 49970e (1968).
Kamihara et al., "Pyruvate Oxidation and Related Metabolism in *Streptococcus faecalis*, III, Effects of Cultural Conditions on Growth in a Lipid Deficient Medium", *Chem. Abst.*, vol. 71, No. 21, p. 94, Abs. No. 99136y (1969).
"American Type Culture Collection Catalogue of Strains", 12th Ed., Rockville, Md., (1976), p. 118.

*Primary Examiner*—Thomas G. Wiseman
*Attorney, Agent, or Firm*—Ronald P. Hilst

[57] ABSTRACT

An improved process for producing α-glycerophosphate oxidase provides yields of more than 1500 U per liter. The enzyme is produced by growing a member of the family Lactobacillaceae in a medium comprising pyruvate and an inducer for α-glycerophosphate oxidase. In the preferred embodiment, a medium comprising a mixture of glucose and pyruvate as carbon sources provides a synergistic effect on the production of α-glycerophosphate oxidase.

18 Claims, 1 Drawing Figure

□ – DISSOLVED OXYGEN

▲ – pH

△ – DRY CELL WEIGHT

○ – α-GLYCEROPHOSPHATE OXIDASE

PROCESS FOR THE PRODUCTION OF α-GLYCEROPHOSPHATE OXIDASE

This is a continuation-in-part of our co-pending application Ser. No. 749,650, filed Dec. 10, 1976, now abandoned.

FIELD OF THE INVENTION

This invention relates to processes for producing α-glycerophosphate oxidase, and particularly to such processes comprising the cultivating of *Streptococcus faecalis* ATCC 12755.

BACKGROUND OF THE INVENTION

α-Glycerophosphate oxidase and useful techniques for its preparation and extraction have been described by Koditschek, L. K. and Umbreit, W. W., "α-Glycerophosphate Oxidase in *Streptococcus faecium* F24", Journal of Bacteriology, Vol. 98, No. 3, P. 1063–68 (1969) and by Jacobs, N. J. and Van Demark, P. J., "The Purification and Properties of the α-Glycerophosphate Oxidizing Enzyme of *Streptococcus faecalis,* 10Cl," Archives of Biochemistry and Biophysics, Vol. 88, p. 250–55 (1960). The enzyme is useful for the oxidation of α-glycerophosphate in the presence of oxygen to produce dihydroxyacetone phosphate and hydrogen peroxide.

Koditschek and Umbreit, supra, described the properties of α-glycerophosphate oxidase in *Streptococcus faecium* F24 using for their study various assay techniques including the manometric assay. Cultures of *Streptococcus faecium* were maintained on stabs of AC agar consisting of 1% tryptone, 1% yeast extract, 0.5% $K_2HPO_4$, 0.1% g glucose and 1.5% agar (sometimes referred to as AC medium below). The cells were separated from this medium and enzyme preparations were extracted for assay.

Jacobs and Van Demark, supra, who also used manometric assay techniques in their study, describe the properties of α-glycerophosphate oxidase in *Streptococcus faecalis* 10Cl. They grew the *Streptococcus faecalis* in an AC medium as described above but having 0.2% glucose. They report that the enzyme from *Streptococcus faecalis* is highly specific for L-α-glycerophosphate as a substrate with no demonstrable activity on β-glycerophosphate, glycerol, dihydroxyacetone phosphate, or 1,2-propanediol phosphate.

Jacobs, N. J. and Van Demark, P. J. in an article "Comparison of the Mechanism of Glycerol Oxidation in Aerobically and Anaerobically Grown *Streptococcus faecalis*", Journal of Bacteriology, Vol. 79, pp. 532–538 (1960) discuss the metabolism of glycerol in taxonomic studies using aerobically and anaerobically grown cells from *Streptococcus faecalis*. The *Streptococcus faecalis* was grown in the standard AC medium described above.

Gunsalus, I. C., and Umbreit, W. W., "The Oxidation of Glycerol by *Streptococcus Faecalis*", Journal of Bacteriology, 49, 347–357 (1945) report on assay studies of the oxidation of glycerol by active cell suspensions of *Streptococcus faecalis*. They found that the addition of pyruvate to the assay would allow the oxidation of higher levels of glycerol because pyruvate acts as a scavenger for $H_2O_2$. α-Glycerophosphate oxidase activity was not noted.

Gunsalus, I. C., "Products of Anaerobic Glycerol Fermentation by *Streptococcus Faecalis*", Journal of Bacteriology, 54, 239–244 (1947) reports on the growth of *Streptococcus faecalis* in a medium containing glycerol and up to 1% yeast extract. Gunsalus describes the growth of *Streptococcus faecalis* with glycerol as slight (aerobic growth) or poor (anaerobic growth).

Claridge, C. A. and Hendlin, D., "Oxidation of Glycerol by *Streptococcus Faecalis*", Journal of Bacteriology, Vol. 84, p. 1181–86 (1962) describe studies of the utilization of glycerol by *Streptococcus faecalis* made using conventional warburg assays. They suggest growing *Streptococcus faecalis* in a medium containing 1 g/liter glucose supplemented with 1% glycerol (10 g/liter) in order to obtain cells that will rapidly oxidize glycerol in their assay. α-Glycerophosphate oxidase activity was not noted.

The references discussed above generally describe studies relating to the oxidation of glycerol. Only the first two of these references, "Koditschek and Umbreit" and "Jacobs and Van Demark", indicate the presence of α-glycerophosphate oxidase in their assays. Neither suggest that growing bacterium on a combination of (1) pyruvate, (2) an inducer for α-glycerophosphate oxidase and, preferably, (3) glucose will produce unexpectedly high yields of α-glycerophosphate oxidase. None of the other references even suggest the presence of α-glycerophosphate oxidase in their strains of microorganisms.

SUMMARY OF THE INVENTION

According to the present invention, high yields of α-glycerophosphate oxidase are obtained by growing a member of the family Lactobacillaceae, preferably *Streptococcus faecalis*, in a medium containing (1) pyruvate as a carbon source, and (2) an inducer for α-glycerophosphate oxidase. In addition to the above ingredients, it is preferred that the medium also contain glucose. The medium may also beneficially comprise yeast extract, tryptone and $K_2HPO_4$. In the preferred embodiment of the invention the medium containing a mixture of glucose and pyruvate as carbon sources has a synergistic effect on the production of α-glycerophosphate oxidase. In a more preferred embodiment of the invention, inorganic salts and vitamins are added to the medium to significantly increase the yield of α-glycerophosphate oxidase.

FIG. 1 illustrates the kinetics associated with the production of α-glycerophosphate oxidase in a 150 liter fermentor according to the present invention.

Among the species within the family Lactobacillaceae which can be employed in the practice of this invention are: from the genus Streptococcus: *S. faecalis, S. cremoris, S. faecium, S. salivarius;* from the genus Lactobacillus: *L. plantarum, L. casei, L. delbrueckii, L. fermentum, L. pentoaceticus, L. lactis, L. buchneri, L. leichmannii;* from the genus Leuconostoc: *L. mesenteroides;* and from the genus Pediococcus: *P. cerevisiae.*

Of the above-noted species, *S. faecalis* (*S. faecium*) is preferred and most preferred, is *S. faecalis* ATCC 12755.

DESCRIPTION OF THE INVENTION

Streptococci are commonly grown in a medium called "STP Medium" herein, which is described by Wood, A. J. and Gunsalus, I. C., "The Production of Active Resting Cells of Streptococci", Journal of Bacteriology, Vol. 44, p. 333–41 (1942). When growing *Streptococcus faecalis* ATCC 12755 in the STP Medium, which is described below, 60-80 U per liter of α-glycerophosphate oxidase is produced.

The microoganism mentioned in the preceding paragraph and elsewhere in this specification is that which was originally submitted to the American Type Culture Collection as *Streptococcus faecalis* ATCC 12755 and which was listed in their catalog under that name up to the Eleventh Edition in 1974. This same strain was renamed *Streptococcus faecium* ATCC 12755 in the Twelfth Edition of the Catalog.

In accordance with the present invention, high yields of α-glycerophosphate oxidase are obtained by growing microoganisms from the family Lactobacillaceae, especially *Streptococcus faecalis*, in STP Medium modified by the addition of pyruvate and, preferably, glucose as carbon sources and of an inducer for α-glycerophosphate oxidase. The addition of glycerol as the inducer has been found to increase the yield of α-glycerophosphate oxidase by as much as 3 times that obtained without glycerol. Other useful α-glycerophosphate oxidase inducers are glycerol analogues which include, for example, 3-methyl-1,2-propanediol; 1,3-propanediol; 1,2-propanediol,; 2,3-butanediol; 1,2,4-butanetriol; monoacetin; 1-monopropionin; 1-monobutyrin; monostearin; monoolein; and trilaurin.

A useful amount of inducer has generally been found to be in the range of from about 1.0 to 10 grams per liter of medium. Preferably about 2.0 to 5.0 grams per liter of inducer is used.

The STP Medium as described by Wood and Gunsalus contains glucose—1.0 g/liter; yeast extract—10 g/liter; tryptone—10 g/liter; and $K_2HPO_4$—5 g/liter. Useful ranges for these ingredients have been found to be: glucose, about 0.1 to 3.0 g/liter; yeast extract, about 1.0 to 20 g/liter, preferably about 2.0 to 10 g/liter; tryptone, about 5 to 20 g/liter; and $K_2HPO_4$, at least about 3.0 g/liter, preferably 3.0 to about 5.0 g/liter.

Other protein hydrolysates which can be substituted for tryptone in the growth medium include, for example, Soy Peptone Type T, Edamin (Type T), Ferm Amine Types I, II, III and IV, N-Z Amine Types AT, BT, ET and YTT, all available from Sheffield Chemical Div. of Kraftco Corp.; Union, NJ; Casein Hydrolysate; Anatone, Microbiotone, and Pharmatone, available from Cudahy Laboratories, Omaha, Neb.; Pharmamedia available from traders Protin Div. Traders Oil Mill Co., Fort Worth, Tex. and ammonium sulfate. It will be appreciated, however, that when one of the above protein hydrolysates is substituted for tryptone in the growth medium, the optimum amount of such protein hydrolysate may be somewhat more or less than the optimum amount of tryptone. A particularly useful substitute for tryptone is the Soy Peptone Type T which has increased yields of α-glycerophosphate oxidase to more than 5 times that obtained when using tryptone.

Other useful carbon sources which can be substituted into the growth medium in place of glucose include, for example, citric acid, lactic acid sodium acetate, sodium succinate, aspartic acid, glutamic acid, corn syrup, molasses, fructose, lactose, maltose, and sucrose.

In a most preferred embodiment of the invention, about 0.5 to about 3.0 g/liter of glucose and about 0.5 to about 2.0 g/liter of sodium pyruvate are added to the growth medium. The combination of glucose and sodium pyruvate in the growth medium appears to have a synergistic effect on the yield of α-glycerophosphate oxidase. When using this combination of carbon sources, the yield of enzyme has been increased up to 8 times that obtained when using 1 gm/liter of glucose as the carbon source.

It has also been found advantageous to add an effective amount of inorganic salts and vitamins to the growth medium. As used herein, the term "effective amount" means a sufficient amount of inorganic salts and vitamins added to the growth medium to increase the yield of enzyme. The exact amount of such salts and vitamins to add depends upon the types of salts and vitamins. This quantity is generally small and can easily be determined by those having skill in the art by routine testing.

When growing microorganisms such as *Streptococcus faecalis* to produce high yields of enzyme in a large scale fermentor, foaming is often encountered. In order to control the foaming, especially when producing large batches of enzyme, use of a foam control agent is advisable. One such foam control agent found useful in the practice of this invention is Polyglycol P-2000, available from Dow Chemical Co. (Midland, Mich.). Up to 0.5 g/liter of this foam control agent can be used in the growth medium without inhibiting the production of enzyme. Generally, however, about 0.1 g/liter has been found sufficient to control foaming. Other foam control agents can also be used; the main criterion for selection and use being the lack of inhibition of enzyme synthesis at a concentration level that will control the foam.

The microorganism can be grown over a reasonable range of temperatures to produce α-glycerophosphate oxidase. Good results can be obtained in a temperature range of 25°–42° C. Best results have been achieved at a temperature of about 30° C. After the cells have been grown, the α-glycerophosphate oxidase can be extracted by means of conventional techniques.

In the following examples which are presented to better demonstrate the successful practice of the invention, the following definitions apply:

1. Culture

*Streptococcus faecalis* ATCC 12755 was used for all the experiments described.

2. Media (a) Culture maintenance medium. Micro Assay Culture agar (Difco Laboratories, Detroit, Mich.) with 0.2% glycerol was used for the culture maintenance.

| b) Fermentation media | g/liter |
| --- | --- |
| i. STP Medium (Wood and Gunsalus, 1942) | |
| Glucose | 1.0 |
| Yeast extract | 10.0 |
| Tryptone | 10.0 |
| $K_2HPO_4$ | 5.0 |
| Distilled water to 1 liter | |

| ii. Modified STP Medium - 1 | g/liter |
| --- | --- |
| Glucose | 1.0 |
| Tryptone | 10.0 |
| Yeast extract | 10.0 |
| $K_2HPO_4$ | 5.0 |
| Glycerol | 2.0 |
| Distilled water to 1 liter | |

| iii. Modified STP Medium - 2 | g/liyter |
| --- | --- |
| Sodium pyruvate | 2.0 |
| Yeast extract | 2.0 |
| Tryptone | 10.0 |
| $K_2HPO_4$ | 5.0 |
| Glycerol | 2.0 |
| Distilled water to 1 liter | |

| iv. Modified STP Medium - 3 | g/liter |
|---|---|
| Sodium pyruvate | 2.0 |
| Yeast extract | 2.0 |
| Tryptone | 10.0 |
| K$_2$HPO$_4$ | 5.0 |
| Glycerol | 2.0 |
| Salt solution C | 5.0 |
| Vitamin solution | 1.0 |
| Distilled water to 1 liter | |

| v. Modified STP Medium - 4 | g/liter |
|---|---|
| Sodium pyruvate | 2.0 |
| Yeast extract | 2.0 |
| Tryptone | 10.0 |
| K$_2$HPO$_4$ | 5.0 |
| Glycerol | 2.0 |
| Salt solution PYS | 20 ml |
| Vitamin solution | 1.0 ml |
| Distilled water to 1 liter | |

| vi. Modified STP Medium - 5 | g/liter |
|---|---|
| Glucose | 2.0 |
| Sodium Pyruvate | 2.0 |
| Yeast extract | 2.0 |
| Tryptone | 10.0 |
| K$_2$HPO$_4$ | 5.0 |
| Glycerol | 2.0 |
| Salt solution PYS | 20.0 ml |
| Vitamin solution | 1.0 ml |
| Distilled water to 1 liter | |

| vii. Modified STP Medium - 6 | g/liter |
|---|---|
| Sodium Pyruvate | 2.0 |
| Yeast extract | 2.0 |
| Tryptone | 10.0 |
| K$_2$HPO$_4$ | 5.0 |
| Glycerol | 2.0 |
| Salt solution PYS | 5 ml |
| Vitamin solution | 1 ml |
| Distilled water to 1 liter | |

| viii. Modified STP Medium - 7 | g/liter |
|---|---|
| Sodium Pyruvate | 2.0 |
| Yeast extract | 2.0 |
| Tryptone | 10.0 |
| K$_2$HPO$_4$ | 5.0 |
| Glycerol | 2.0 |
| Salt solution PYS | 2.5 ml |
| Vitamin solution | 1 ml |
| Tap water to 1 liter | | c) Salt solutions:

i. Salt Solution A

Part 1 and Part 2 were added in equal volumes to give salt solution A.

| Part 1 | g/liter of 0.1N HCl |
|---|---|
| MgSO$_4$.7H$_2$O | 100.0 |
| FeSO$_4$7H$_2$O | 10.0 |
| MnSO$_4$.H$_2$O | 1.0 |
| NaMoO$_4$.2H$_2$O | 0.5 |
| 0.1N HCl to 1 liter | |
| Part 2 | |
| CaCl$_2$ | 10.0 |
| Distilled water to 1 liter | | ii. Salt Solution C

| | g/liter of 0.1N HCl |
|---|---|
| MgSO$_4$.7H$_2$O | 25.0 |
| CaCl$_2$.2H$_2$O | 0.1 |
| FeSO$_4$.7H$_2$O | 2.8 |
| MnSO$_4$.H$_2$O | 1.7 |
| ZnSO$_4$.7H$_2$O | 0.06 |
| NaCl | 0.6 | iii. Salt Solution PYS

| | g/liter |
|---|---|
| Na$_3$C$_6$H$_5$O$_7$.2H$_2$O [Sodium citrate] | 5.0 |
| MnCl$_2$.4H$_2$O | 3.0 |
| ZnCl | 2.0 |
| FeCl$_3$.6H$_2$O | 2.0 |
| MgCl$_2$.6H$_2$O | 50.0 |
| CuCl$_2$.2H$_2$O | 0.2 |
| CaCl$_2$.2H$_2$O | 0.75 |
| CoCl$_2$.2H$_2$O | 0.2 |
| NaMoO$_4$.2H$_2$O | 0.1 |
| Na$_2$B$_4$O$_7$.10H$_2$O | 0.1 |
| Distilled water to 1 liter | |

| d) Vitamin Solution | mg/liter |
|---|---|
| Thiamine.HCl | 200 |
| p-Aminobenzoic acid | 200 |
| Pyridoxin.HCl | 200 |
| Riboflavin | 200 |
| D-Panthothenic acid (calcium salt) | 200 |
| Folic acid | 2.0 |
| Biotin | 2.0 |

Riboflavin goes into solution on warming. The vitamin solution was filter-sterilized and was added to the medium after sterilization.

(e) In all large scale fermentations, the media also contained 0.01% polyglycol P-2000 as a foam control agent.

3. Maintenance of Culture:

The culture was maintained on the stabs of Micro assay culture agar with 0.2% glycerol; it was transferred to a fresh stab at least once every week. After 48 hours of incubation at 30° C., the stabs were stored at 4° C. Another process used for the preservation of the organism was the storage in liquid nitrogen. For this purpose, the culture was grown in STP medium for 20 hours. The cells were then separated and resuspended in sterile 10% aqueous glycerol with Allen's salt solution (Allen, M. B., Archives of Mikrobiology, Vol. 32, p. 270–277 (1959). A small volume, 0.5–2.0 ml, of this suspension was added to a sterile glass ampoule which was then sealed and stored in liquid nitrogen.

4. Small Scale Fermentation:

(a) Preparation of inoculum—The culture grown on Micro assay culture agar for 48 hours was transferred to 50 ml of STP medium or Modified STP medium-2 in a 250 ml Erlenmeyer flask. The flask was shaken at 30° C. and 200 RPM. After 20 hours of incubation, the contents were centrifuged in a Sorvall refrigerated centrifuge (Model RC IIB, DuPont Instruments Co., Newtown, Connecticut) at 12,000 X g for 15 minutes at 4° C. The supernate was discarded, and the cells were resuspended in the same volume of sterile water as the original. This suspension was used as inoculum.

(b) Production of the enzyme—Twenty-five ml of fermentation medium in a 250 ml Erlenmeyer flask was inoculated with 1.5 ml of inoculum prepared as described in (4.a). The flasks were shaken at 200 RPM at 30° C. After shaking the flasks for 20 hours, 2.5 ml of sample were withdrawn from each flask. The samples were centrifuged at 19,000 X g for 15 minutes in a Sorvall refrigerated centrifuge. The cells were resuspended in 2.5 ml of deionized water. This suspension was diluted 10 fold. The diluted suspension was used for the determination of dry cell weight and for the assay of α-glycerophosphate (α-GP) oxidase.

5. Large Scale Fermentation:

(a) Preparation of inoculum The inoculum for 150-liter fermentor was prepared by three different methods.

(1) Six 2.8-liter Fernbach flasks containing 500 ml of Modified STP Medium-2 were inoculated with Streptococcus faecalis ATCC 12755, grown for 48 hours on stabs of Micro assay culture agar with 0.2% glycerol. One stab was used to inoculate each Fernbach flask. The flasks were shaken at 125 RPM and at 30° C. After incubation for 20 hours, the contents of the flasks were aseptically centrifuged at 6000 x g in a refrigerated centrifuge (Model RC IIB, DuPont Instrument Co., Newtown, Conn.) for 15 min. The supernatant liquid was discarded, and the cell pellet was resuspended in sterile distilled water. A total volume of 500 ml of distilled water was used to resuspend the cells from 6 flasks. This cell suspension was used to inoculate a 150-liter fermentor.

(2) The procedure was the same as above except that the contents of the flasks were not centrifuged. The whole fermentation broth from 6 flasks was used to inoculate a 150-liter fermentor.

(3) This method of inoculum preparation was used to prepare inoculum in most of the experiments reported herein. A 250 ml Erlenmeyer flask containing 50 ml of Modified STP Medium-2 was inoculated with *Streptococcus faecalis* ATCC 12755 grown for 48 hours on a stab of Micro assay culture agar with added 0.2% glycerol. The flask was shaken at 200 RPM and at 30° C. After shaking for 12 hours, the contents of the flask were used to inoculate a 14-liter fermentor. Prior to the inoculation, this fermentor was charged with 10 liters of desired fermentation medium and was sterilized for 1 hour. The medium was cooled to 30° C. and inoculated as described above. The medium was agitated with 3 flat-bladed turbine impellers at 1300 RPM. A ring sparger was used for aeration. The air flow rate was 0.2 VVM (volumes of air per volume of media per minute) or 2 liters per minute. This gave us a mass transfer coefficient, $K_L.a$, of 8 min$^{-1}$. The temperature was maintained at 30° C. After 12 hours, the whole broth was used to inoculate a 150-liter fermentor. The purity of the culture was monitored throughout the development of inoculum. Microscopic examination and plating technique were used for this purpose.

(b) Production of α-GP oxidase

A 150-liter fermentor was charged with 100 liters of appropriate fermentation medium and was sterilized for one hour. The medium was cooled to 30° C. It was inoculated by aseptically transferring the contents of the 14-liter fermentor prepared as described in method 3 above. The medium was agitated with 3 flat-bladed turbine impellers at 250 RPM and aerated with a ring sparger. The rate of aeration was 0.18 VVM or 20 liters of air/min. Under these conditions, the value of $K_L.a$ was 1.15 min$^{-1}$. The temperature was kept at 30° C. Samples were aseptically withdrawn every hour with an automatic sampler (New Brunswick Scientific Co., Inc., New Brunswick, N.J.), and the cell growth as well as α-GP oxidase production was measured. Dissolved oxygen concentration was monitored with a membrane electrode (IL 530, Industrial oxygen measuring system, Sensorlabs, Division of Instrumentation Laboratories, Inc., Lexington, Mass.). We also measured pH with an Ingold electrode (Type 764-31B, Dr. W. Ingold Ltd., Zurich, Switzerland). The fermentor was cooled to 10° C. with cold water when the enzyme level reached the desired value and the cells were harvested in a refrigerated continuous centrifuge (Cepa centrifuge Model Z81G, Carl Padberg GMBH, West Germany). Average fermentation time was 9-10 hours.

6. Determination of Dry Cell Weight:

A calibration curve correlating dry cell weight to absorbance at 660 nm was prepared. The absorbance was measured on a Spectronic 20 Spectrophotometer (Bausch and Lomb, Rochester, N.Y.), and the dry cell weight was computed from the calibration curve.

7. Assay of α-Glycerophosphate Oxidase Activity:

The α-GP oxidase activity was determined by measuring the peroxidase-catalyzed oxidation of a leuco dye by $H_2O_2$ released during the oxidation of α-glycerophosphate by α-GP oxidase. One unit of enzyme activity (U) was defined as that amount of the enzyme which converts 1 μmole of substrate into product per minute at 37° C. and at pH 7.0.

(a) Reagents (i) KP buffer: 0.1 M potassium phosphate buffer, pH 7.0.

(ii) Substrate solution: Dissolve 17.288 g of α-glycerophosphate in 100 ml of KP buffer.

(iii) Dye solution: Dissolve 1 g of 3,3'-dimethoxybenzidine dihydrochloride (O-dianisidine) in 100 ml of deionized water.

(iv) Detergent solution: Dissolve 1 g of Triton X-100 (a polyethoxy ethylene surfactant commercially available from Rohm & Haas, Phila., Pa) in 10 ml. of KP buffer.

(v) Buffer solution: Dissolve 3.3 mg of horseradish peroxidase type II in 50 ml of KP buffer. Add 1.1 ml of dye solution and 6.6 ml of detergent solution. Make the volume to 100 ml with KP buffer.

(b) Procedure

Six ml of buffer solution and 1 ml of substrate solution in a test tube were equilibrated at 37° C. for 15 minutes in a waterbath shaker (New Brunswick Scientific, New Brunswick, N.J.). The samples were diluted to contain 5-25 mU of α-GP oxidase per ml. One ml of appropriately diluted sample was added to the equilibrated tubes. A blank was prepared with 1 ml of deionized water in place of the sample. The tubes were shaken at 37° C. in a water bath shaker. The color development was measured every 5 minutes with a Spectronic 20 Spectrometer at 430 nm for 1 hour. The extinction coefficient was determined for the dye and was used to convert the optical density into concentration of the substrate utilized.

8. Determination of Mass Transfer Coefficient ($K_L.a$)

The mass transfer coefficient was measured by monitoring the dissolved oxygen concentration and the outlet oxygen concentration. The dissolved oxygen concentration was determined with a membrane electrode as described in paragraph 5.(b) (Production of α-GP oxidase) above. The outlet oxygen concentration was measured with a paramagnetic analyzer (Type CA150, Servomex Controls Ltd., Crowborough, Sussex, Eng). The following relationship was used to calculate $K_L.a$.

$$N_A = K_L \cdot a (C^* - C_L)$$

wherein:

$N_A$ = Rate of mass transfer
$K_L$ = Mass transfer coefficient
$a$ = Interfacial area
$C^*$ = Saturation concentration of dissolved oxygen
$C_L$ = Instantaneous dissolved oxygen concentration Examples 1-5 demonstrate the use of small scale techniques as described above.

EXAMPLE 1

Inductive Effect of Glycerol

The addition of glycerol had a dramatic effect on the production of the enzyme. The maximum production was obtained in the medium containing 2 g of glycerol per liter (Table 1). Further increase in glycerol concentration did not increase the yield of the enzyme. The growth of the culture was not affected to a great extent; at most, a 20% increase in the dry cell weight was noted, whereas there was a more than 3-fold increase in the enzyme yield.

Table 1

| Concentration of Glycerol | Dry Cell Weight | Production of α-GP Oxidase | |
|---|---|---|---|
| g/liter | g/liter | U/liter | % of Control |
| 0.0[a] | 0.34 | 62 | 100 |
| 2.0 | 0.41 | 205 | 330 |
| 5.0 | 0.38 | 203 | 328 |
| 10.0 | 0.34 | 178 | 287 |

[a]Control
The culture was grown in STP Medium supplemented with glycerol at concentrations shown in the table.

EXAMPLE 2

Effect of Carbon Sources a. Effect of glucose—As shown in Table 2, the growth of the culture was strongly dependent on the concentration of glucose. A three-fold increase in the dry cell weight was obtained when 3 g of glucose per liter was added to the medium as compared to that obtained in medium without glucose. The concentration of glucose also had a significant effect upon the production of α-GP oxidase; omission of glucose from the medium caused a 38% reduction in production. The production of the enzyme increased with increasing glucose concentration up to 1.0 g per liter. Further increase in the concentration of glucose caused repression of α-GP oxidase synthesis.

Table 2

| Concentration of Glucose | Dry Cell Weight | α-GP Oxidase Production | |
|---|---|---|---|
| g/liter | g/liter | U/liter | % of Control |
| 0 | 0.22 | 52 | 62 |
| 0.5 | 0.29 | 62 | 76 |
| 1.0[a] | 0.32 | 82 | 100 |
| 2.0 | 0.57 | 30 | 36 |
| 3.0 | 0.61 | 39 | 47 |

[a]Control

The culture was grown in STP Medium as described hereinabove. The concentration of glucose was varied as indicated in the table.

b. Effect of sodium pyruvate—The replacement of glucose with sodium pyruvate considerably improved the growth and the production of α-GP oxidase as shown in Table 3. However, high concentrations of pyruvate (>3 g/liter) reduced the production of the enzyme. The optimum concentration of 2.0 g/liter replaced glucose as a carbon source in the Modified STP Media 2, 3, 4. The organism was grown on Modified STP Medium-1 as described hereinabove except that the glucose in the medium was replaced with sodium pyruvate at concentrations shown in the table.

Table 3

| | Effect of Sodium Pyruvate | | | |
|---|---|---|---|---|
| Carbon Source | Concentration of Carbon Source g/liter | Dry Cell Weight g/liter | Production of α-GP Oxidase | |
| | | | U/liter | % of Control |
| None | 0.0 | 0.19 | 176 | 88 |
| Glucose[a] | 1.0 | 0.33 | 199 | 100 |
| Sodium pyruvate | 0.5 | 0.36 | 352 | 176 |
| Sodium pyruvate | 1.0 | 0.46 | 386 | 193 |
| Sodium pyruvate | 2.0 | 0.60 | 484 | 242 |
| Sodium pyruvate | 5.0 | 0.55 | 314 | 157 |

[a]Control c. Combined effect of glucose and sodium pyruvate—It was observed that the combined addition of 2.0 g/liter of glucose and 2.0 g/liter of pyruvic acid sodium salt increased the growth of the culture and, surprisingly, greatly increased the production of enzyme at the same time as shown in Table 4. This modification, called Modified STP Medium 5, represents a preferred medium for the present invention.

Table 4

| | Effect of Supplementation with Glucose | | | |
|---|---|---|---|---|
| Concentration of Glucose g/liter | Concentration of Pyruvic Acid Sodium Salt g/liter | Dry Cell Weight g/liter | α-GP Oxidase Production | |
| | | | U/liter | % of Control |
| 0 | 0 | 0.33 | 237 | 30 |
| 0 | 0.5 | 0.48 | 314 | 40 |
| 0 | 1.0 | 0.63 | 384 | 48 |
| 0 | 2.0[a] | 0.58 | 794 | 100 |
| 0.5 | 0 | 0.51 | 282 | 36 |
| 0.5 | 0.5 | 0.68 | 412 | 52 |
| 0.5 | 1.0 | 0.80 | 580 | 73 |
| 0.5 | 2.0 | 0.74 | 1052 | 133 |
| 1.0 | 0 | 0.49 | 194 | 24 |
| 1.0 | 0.5 | 0.81 | 500 | 63 |
| 1.0 | 1.0 | 0.81 | 540 | 68 |
| 1.0 | 2.0 | 0.79 | 1069 | 135 |
| 2.0 | 0 | 0.62 | 418 | 53 |
| 2.0 | 0.5 | 0.95 | 490 | 62 |
| 2.0 | 1.0 | 0.99 | 651 | 82 |
| 2.0 | 2.0 | 1.00 | 1539 | 194 |
| 3.0 | 0 | 0.72 | 27 | 3 |
| 3.0 | 0.5 | 1.05 | 315 | 40 |
| 3.0 | 1.0 | 1.13 | 369 | 46 |
| 3.0 | 2.0 | 1.06 | 998 | 123 |

[a]Control
The culture was grown on Modified STP Medium-4 with the above concentrations of glucose and pyruvic acid sodium salt.

EXAMPLE 3

Effect of Vitamins

Vitamins stimulated the enzyme production by as much as 30%, though there was no effect on the growth of the culture (Table 5). It was also shown that the increase in the enzyme production was not proportional to the increase in the concentration of vitamins.

Table 5

| | Effect of Vitamins | | |
|---|---|---|---|
| Volume of Vitamin Solution Added ml/liter | Dry Cell Weight g/liter | α-GP Oxidase Production | |
| | | U/liter | % of Control |
| 0.0[a] | 0.64 | 766 | 100 |
| 1.0 | 0.63 | 808 | 106 |
| 2.0 | 0.66 | 939 | 123 |
| 3.0 | 0.63 | 882 | 116 |
| 5.0 | 0.62 | 908 | 119 |

Table 5-continued

Effect of Vitamins

| Volume of Vitamin Solution Added ml/liter | Dry Cell Weight g/liter | α-GP Oxidase Production U/liter | % of Control |
| --- | --- | --- | --- |
| 10.0 | 0.65 | 1011 | 133 |

[a]Control

The culture was grown in Modified STP Medium-3. The concentration of vitamin solution was changed as shown in the table. For the composition of the vitamin solution, refer to paragraph 2. (d) Vitamin Solution above.

EXAMPLE 4

Effect of Inorganic Salts

The stimulation of enzyme production by the addition of trace elements indicated that trace elements may be the other limiting nutrient(s) in our fermentation medium. Trace elements are those which the culture requires in very small, trace quantities, on the order of parts per million, or less. The culture required a number of elements in trace amounts, and as more of these were supplied, the better the enzyme yields became. Tables 6A, 6B and 6C illustrate that salt solution PYS, which contains more trace elements than salt solution C, was better than salt solution C in improving α-GP oxidase production. Salt solution C, in turn, was better than salt solution A for the same reason.

Table 6A

Effect of Various Mixtures of Trace Elements: Effect of Salt Solution C

| Volume Added of Salt Solution C ml/liter | Dry Cell Weight g/liter | α-GP Oxidase Production U/liter | % of Control |
| --- | --- | --- | --- |
| 0.0[a] | 0.49 | 439 | 100 |
| 0.5 | 0.62 | 630 | 143 |
| 1.0 | 0.59 | 598 | 136 |
| 2.5 | 0.60 | 669 | 152 |
| 5.0 | 0.61 | 729 | 165 |
| 10.0 | 0.64 | 747 | 170 |

[a]Control

The culture was grown on Modified STP Medium-2, supplemented with salt solution C in concentrations as described in the table.

Table 6B

Effect of Various Mixtures of Trace Elements: Effect of Salt Solution A

| Mixture of Trace Elements Added | Volume Added ml/liter | Dry Cell Weight g/liter | α-GP Oxidase Production U/liter | % of Control |
| --- | --- | --- | --- | --- |
| None[a] | — | 0.57 | 541 | 100 |
| Salt Solution C | 5.0 | 0.57 | 1037 | 192 |
| Salt Solution A | 2.0[b] | 0.61 | 837 | 155 |

[a]Control
[b]Optimum concentration of salt solution A
The medium used in this experiment was Modified STP Medium-2. It was supplemented as shown.

Table 6C

Effect of Various Mixtures of Trace Elements: Effect of Salt Solution PYS

| Mixture of Trace Elements Added | Volume Added ml/liter | Dry Cell Weight g/liter | α-GP Oxidase Production U/liter | % of Control |
| --- | --- | --- | --- | --- |
| None[a] | — | 0.62 | 582 | 100 |

Table 6C-continued

Effect of Various Mixtures of Trace Elements: Effect of Salt Solution PYS

| Mixture of Trace Elements Added | Volume Added ml/liter | Dry Cell Weight g/liter | α-GP Oxidase Production U/liter | % of Control |
| --- | --- | --- | --- | --- |
| Salt Solution C | 5.0 | 0.63 | 811 | 140 |
| Salt Solution PYS | 5.0 | 0.69 | 923 | 158 |
| Salt Solution PYS | 10.0 | 0.70 | 1000 | 171 |
| Salt Solution PYS | 20.0 | 0.67 | 978 | 168 |
| Salt Solution PYS | 50.0 | 0.75 | 1130 | 194 |

[a]Control. These flasks contained Modified STP Medium without salt solution C. Modified STP Medium-3 was used in this experiment. Salt solution C was replaced by salt solution PYS in concentrations shown above.

EXAMPLE 5

Effect of Vitamins and Trace Elements

As described above, the enzyme production increased when the medium was supplemented with either the vitamin mixture or various mixtures of trace elements. A synergistic effect on the enzyme production was observed upon the addition of both the vitamin solution and salt solution C (Table 7). There was no significant effect on the growth of the culture.

Table 7

Effect of Vitamins and Trace Elements

| Additions | Dry Cell Weight g/liter | α-GP Oxidase Production U/liter | % of Control |
| --- | --- | --- | --- |
| None[a] | 0.60 | 530 | 100 |
| 5.0 ml salt solution C per liter | 0.65 | 577 | 109 |
| 1.0 ml vitamin solution per liter | 0.59 | 582 | 110 |
| 5.0 ml salt solution C and 1.0 ml vitamin solution per liter | 0.63 | 811 | 153 |

[a]Control
The culture was grown on Modified STP Medium-2. Additions to the medium were as shown in table.

The following examples demonstrate the use of a 150 liter fermentor employed in the large scale fermentation techniques described above.

EXAMPLE 6

Effect of Size of Inoculum

Three procedures for inoculum preparation, described above, were tested. The size of inoculum (6–10 liters) did not affect the growth of the culture or the production of the enzyme. However, the increase in the size of inoculum did reduce the time required to reach the maximum growth and the enzyme production by 30%. Results, shown in Table 8, indicate that whole broth was a satisfactory inoculum compared to centrifuged and resuspended cells.

Table 8

Effect of Size of Inoculum

| Size of Inoculum | Growth | | α-GP Oxidase | |
| --- | --- | --- | --- | --- |
| | Dry Cell Weight g/liter | Time Required to Reach Maximum Hrs. | Avg. Yield U/liter | Time Required to Reach Maximum Hrs. |
| 6-liters centrifuged | 0.61 | 10.5 | 837 | 11.3 |
| 6-liters uncentrifuged | 0.65 | 9.25 | 787 | 9.25 |
| 10-liters (14-liter | 0.62 | 7.75 | 811 | 7.75 |

Table 8-continued

| | Effect of Size of Inoculum | | | |
|---|---|---|---|---|
| | Growth | | α-GP Oxidase | |
| Size of Inoculum | Dry Cell Weight g/liter | Time Required to Reach Maximum Hrs. | Avg. Yield U/liter | Time Required to Reach Maximum Hrs. |
| fermentor) | | | | |

Modified STP Medium-3 was used in these experiments. The details of the procedure are as described hereinabove.

EXAMPLE 7

Effect of Glycerol

Increasing glycerol concentrations above 2 g/liter did not appear to improve the enzyme yield per liter in flasks or in the large fermentor. However, increasing glycerol concentrations above 2 g/liter did affect the growth of cells in the large fermentor. In contrast to the flask studies, in which growth was not affected, the growth of the culture in the fermentor was increased by 48%, as shown in Table 9. The optimum concentration of glycerol for enzyme synthesis was approximately 2 g/liter.

Table 9

| | Effect of Glycerol | |
|---|---|---|
| Concentration of Glycerol g/liter | Dry Cell Weight g/liter | α-GP Oxidase U/liter |
| 2.0[1] | 0.63 | 1054 |
| 3.0 | 0.93 | 1039 |

[1]Control

Modified STP Medium-6 was used in this 150-liter fermentor experiment. The concentration of glycerol was varied as indicated. The inoculum was prepared in 14-liter fermentor.

EXAMPLE 8

Effect of Glycerol Analogues

We have shown that α-GP oxidase is an inducible enzyme, and that it is induced by glycerol. Since glycerol is a precursor of the substrate, α-glycerophosphate, as well as a readily utilizable carbon source, its concentration must reduce during the fermentation. Therefore, it would be useful to find an inducer whose concentration did not decrease during the fermentation, i.e., a gratuitous inducer. For this purpose, we tested a number of glycerol analogues and monoglycerides. The following experiments were carried out in shake flasks. Induction of α-GP oxidase was obtained with all of the glycerol analogues tested (Table 10). The enzyme level was reduced to 38% of the control when glycerol was eliminated from the medium. This level was increased to 50% of the control when the glycerol analogues, with the exception of ethylene glycol, were added. Ethylene glycol strongly repressed the enzyme synthesis.

Table 10

| | Effect of Glycerol Analogues | | |
|---|---|---|---|
| Glycerol Analogues[a] | Concentration M | Dry Cell Weight g/l | α-GP Oxidase Production % of Control |
| None | — | 0.31 | 38 |
| Glycerol[b] | 0.002 | 0.11 | 100 |
| Ethylene glycol | 0.032 | 0.30 | 17 |
| 3-methoxy 1,2.propanediol | 0.019 | 0.30 | 49 |
| 1,3-propanediol | 0.026 | 0.30 | 42 |
| 1,2-propanediol | 0.026 | 0.30 | 47 |
| 2,3 butanediol | 0.022 | 0.30 | 52 |
| 1,2,4-butanetriol | 0.019 | 0.31 | 49 |
| monoacetin | 0.015 | 0.40 | 98 |
| 1-monopropionine | 0.13 | 0.38 | 70 |
| 1-monobutyrin | 0.012 | 0.37 | 92 |
| monostearin | 0.006 | 0.34 | 34 |
| monoolein | 0.006 | 0.28 | 41 |
| Trilaurin | 0.003 | 0.32 | 46 |

[a]All of the glycerol analogues were tested at 2.0 g/l.
[b]Control
The culture was grown in Modified STP Medium-1 with 2 g yeast extract per liter. Glycerol was substituted with the above.

EXAMPLE 9

Effect of Temperature

A reduction in fermentation temperature from 30° C. to 25° C. reduced the enzyme production by 22% and only slightly increased the growth. The temperature down-shift, however, had a dramatic effect on the time required to reach the maximum growth and the enzyme production; it took twice as long at 25° C. as it did at 30° C. (Table 11).

Table 11

| | Effect of Temperature | | | |
|---|---|---|---|---|
| | Growth | | α-GP Oxidase | |
| Temperature °C. | Dry Cell Weight g/liter | Time Required to Reach Maximum Hrs. | Average Yield U/liter | Time Required to Reach Maximum Hrs. |
| 30[1] | 0.63 | 6.5 | 1054 | 6.5 |
| 25 | 0.71 | 12.0 | 822 | 13.0 |

[1]Control
The medium used was Modified STP Medium-6. The size of inoculum was 10 liters.

EXAMPLE 10

Effect of Change of Nitrogen Source

We have evaluated alternate nitrogen sources to replace tryptone. Trypticase peptone was found to be a good substitute. The α-GP oxidase production in the medium with trypticase peptone was comparable to that in the medium with tryptone, although it did not support the growth of S. faecalis as well. Results are shown in Table 12. These experiments were carried out in shake flasks.

Table 12

| Effect of Change of Manufacturer of Nitrogen Source | | | |
|---|---|---|---|
| Nitrogen Source | | Dry Cell Weight | α-GP Oxidase |
| Generic Name | Trade Name | g/liter | U/liter |
| Trypsin digest casein | Tryptone* | 0.63 | 755 |
| Pancreatic digest of casein | Trypticase peptone** | 0.54 | 788 |

*Product of Difco Laboratories, Detroit Michigan
**Product of BBL, Div. of Becton Dickinson Co., Cockeysville, Maryland
Modified STP Medium-7 was used in these studies. Tryptone was replaced with the same concentration of trypticase peptone. The inoculum was grown in 14-liter fermentor.

EXAMPLE 11

Kinetics of α-GP Oxidase Production

The enzyme production was shown clearly to be growth associated. FIG. 1 shows the growth of the culture at 30° C. in Modified STP Medium-4, the production of α-GP oxidase, dissolved oxygen concentration and pH during the fermentation. Growth reached a maximum in 6 hours; enzyme production reached a maximum in 9 hours. Enzyme concentration remains stable for about 2 hours after reaching maximum. The preferred fermentation time is 6 to 12 hours.

EXAMPLE 12

Various members of the family Lactobacillaceae were evaluated for α-glycerophosphate oxidase production in the medium of Example 7. The results of these evaluations which are shown in Table 13 are reported in terms of units of enzyme produced per liter of medium by cultures grown at 30° C. and 37° C.

TABLE 13

|  | 30° | UL | 37° |
|---|---|---|---|
| Streptococcus faecium, ATCC 12775 | 270 |  | — |
| Streptococcus faecium, ATCC 8043 | 157 |  | 28 |
| Streptococcus faecalis, ATCC 19433 | 143 |  | — |
| Streptococcus cremoris, NRRL B634 | 41 |  | 110 |
| Lactobacillus casei, ATCC 7469 | 116 |  | 107 |
| Lactobacillus delbruckii, NRRL B445 | 141 |  | 54 |
| Lactobacillus fermenti, NRRL B338 | 107 |  | 105 |
| Pediococcus cerevisiae, ATCC 8081 | 33 |  | 41 |
| Pediococcus cerevisiae, ATCC 8043 | 83 |  | 24 |

From Table 13 it is apparent that members of the family Lactobacillaceae produce useful yields of α-glycerophosphate oxidase.

The invention has been described in detail with particular reference to certain preferred embodiments thereof, but it will be appreciated that those skilled in the art can effect modifications within the spirit and scope of the invention.

I claim:

1. A method for producing useful enzyme from a member of the family Lactobacillaceae, said member being capable of producing α-glycerophosphate oxidase, said method comprising growing said member in a nutrient medium comprising pyruvate and an inducer for α-glycerophosphate oxidase and extracting said enzyme.

2. The method of claim 1 wherein the member of the family Lactobacillaceae is selected from the group consisting of Streptococcus faecalis, Streptococcus cremoris, Streptococcus salivarius, Streptococcus faecium, Lactobacillus plantarum, Lactobacillus casei, Lactobacillus delbrueckii, Lactobacillus fermentum, Lactobacillus pentoaceticus, Lactobacillus lactis, Lactobacillus buchneri, Lactobacillus leichmannii, Leuconostoc mesenteroides, and Pediococcus cerevisiae.

3. The method of claim 1 wherein the medium further comprises glucose.

4. A method for producing α-glycerophosphate oxidase by growing Streptococcus faecalis, comprising growing Streptococcus faecalis in a medium comprising pyruvate and an inducer for α-glycerophosphate oxidase to roduce α-glycerophosphate oxidase and extracting the α-glycerophosphate oxidase.

5. The method of claim 4, wherein said inducer is selected from the group consisting of glycerol; 3-methoxy-1,2-propanediol; 1,3-propanediol; 1,2-propanediol; 2,3-butanediol; 1,2,4-butanetriol; monoacetin; 1-monopropionin; 1-monobutyrin; monostearin; monoolein; and trilaurin.

6. The method of claim 4, wherein said inducer is present in an amount of from about 1.0 to about 10 grams per liter of medium.

7. The method of claim 4, wherein the medium comprises from about 0.5 to about 3.0 grams of pyruvate per liter of medium.

8. The method of claim 4, wherein said method includes adding to said medium inorganic salts and vitamins in an amount effective to increase the production of α-glycerophosphate oxidase.

9. The method of claim 8 wherein the inorganic salts are Salt Solution PYS.

10. A method for producing α-glycerophosphate oxidase by growing Streptococcus faecalis, comprising growing cells of Streptococcus faecalis ATCC 12755 in a medium comprising from about 0.5 to about 3.0 grams of pyruvate, from about 2.0 to about 5.0 grams of an α-glycerophosphate oxidase inducer selected from glycerol, monoacetin, or 1-monobutyrin, from about 1.0 to about 20 grams of yeast extract, from about 5 to about 20 grams of a protein hydrolysate, and at least about 3.0 grams of $K_2HPO_4$ per liter of medium; and extracting the α-glycerophosphate oxidase to obtain an α-glycerophosphate oxidase preparation.

11. A method for producing α-glycerophosphate oxidase by growing Streptococcus faecalis, comprising growing Streptococcus faecalis in a medium comprising glucose, pyruvate, and an inducer for α-glycerophosphate oxidase to produce α-glycerophosphate oxidase and extracting the α-glycerophosphate oxidase.

12. The method of claim 11 wherein said inducer is present in an amount of from about 1.0 to about 10 grams per liter of medium.

13. The method of claim 11 wherein the medium comprises from about 0.5 to about 3.0 grams of glucose per liter of medium and from about 0.5 to about 2.0 grams of pyruvate per liter of medium.

14. The method of claim 11 wherein said method includes adding to said medium inorganic salts and vitamins in an amount effective to increase the production of α-glycerophosphate oxidase.

15. The method of claim 14 wherein the inorganic salts are Salt Solution PYS.

16. A method for producing α-glycerophosphate oxidase by growing Streptococcus faecalis, comprising growing cells of Streptococcus faecalis ATCC 12755 in a medium comprising from about 0.5 to about 3.0 grams of glucose, from about 0.5 to about 2.0 grams of pyruvate, from about 2.0 to about 5.0 grams of an α-glycerophosphate oxidase inducer selected from glycerol, monoacetin, or 1-monobutyrin, from about 1.0 to about 20 grams of yeast extract, from about 5 to about 20 grams of a protein hydrolysate, and at least about 3.0 grams of $K_2HPO_4$ per liter of medium; and extracting the α-glycerophosphate oxidase to obtain an α-glycerophosphate oxidase preparation.

17. The method of claim 16 wherein said method includes adding inorganic salts and vitamins to the medium in an amount effective to increase the production of α-glycerophosphate oxidase.

18. The method of claim 16 wherein the method includes controlling the temperature of the medium at about 30° C. while growing the cells.

* * * * *